United States Patent [19]
Bohrer et al.

[11] 3,954,113
[45] May 4, 1976

[54] METHOD OF AND MEANS FOR CLEANING HAIR BETWEEN SHAMPOOS AND METHODS FOR PREPARING SUCH MEANS

[75] Inventors: James Calvin Bohrer, East Brunswick; Gordon Trent Hewitt, Upper Montclair, both of N.J.

[73] Assignee: Colgate-Palmolive Company, New York, N.Y.

[22] Filed: Dec. 14, 1973

[21] Appl. No.: 424,816

[52] U.S. Cl. .................................... 132/7; 424/70
[51] Int. Cl.$^2$ ............................................. A45D 7/00
[58] Field of Search ................. 132/7; 424/16, 70; 252/91; 15/506

[56] References Cited
UNITED STATES PATENTS

| | | | |
|---|---|---|---|
| 2,999,265 | 9/1961 | Duane et al. | 424/16 |
| 3,206,362 | 9/1965 | Hollub | 132/7 |
| 3,335,449 | 8/1967 | Faessinger | 15/506 |
| 3,686,025 | 8/1972 | Russell | 252/91 |

FOREIGN PATENTS OR APPLICATIONS

| | | | |
|---|---|---|---|
| 917,949 | 2/1963 | United Kingdom | 424/70 |

*Primary Examiner*—G. E. McNeill
*Attorney, Agent, or Firm*—Richard N. Miller; Murray M. Grill; Herbert S. Sylvester

[57] ABSTRACT

The method of cleaning hair between shampoos which comprises rubbing the hair with a sheet-like substrate that has been treated to make it electronically attractive to hair soil in the presence of an aqueous liquid in a moistening amount.

Means for cleaning hair between shampoos comprising a sheet-like substrate treated to make it electronically attractive to hair soil and moistened with a cleaning liquid. The substrate is preferably a flexible, absorbent, organic, fibrous sheet having satisfactory wet strength properties such as non-woven fabric and wet strength paper rendered electronically attractive to hair soil by the presence of a cationic organic polyelectrolyte, e.g., by incorporation in a sheet during or impregnation of a sheet after manufacture. The cleaning liquid is aqueous, preferably water and alcohol, usually absorbed in the substrate. Optionally and advantageously the substrate is folded into a compact pad and sealed within a moisture-proof envelope for convenience in carrying and use.

A method of preparing the hair soil removing means comprises treating a suitable substrate to make it electronically attractive to hair soil, e.g., by incorporating in it a substantive cation active agent such as a polyelectrolyte and moistening the substrate with the cleaning liquid. An optional operation is sealing a so-treated and moistened sheet-like substrate within a moisture-proof envelope, preferably using a heat sealable laminate of metal foil, paper and polyethylene layers. Treated sheets of substrate and liquid, however, may be packaged separately and combined at the time of use by moistening the substrate or the hair prior to rubbing the hair with it.

17 Claims, No Drawings

METHOD OF AND MEANS FOR CLEANING HAIR BETWEEN SHAMPOOS AND METHODS FOR PREPARING SUCH MEANS

The present invention relates to a method of and means for cleaning hair between shampoos, and to methods of preparing such means. In greater particularity the method of cleaning hair comprises rubbing it with a sheet-like substrate that has been treated to make it electronically attractive to hair soil in the presence of an aqueous liquid in a moistening amount. The means for cleaning hair comprises a sheet-like fibrous substrate, preferably a flexible, absorbent organic material having satisfactory wet strength characteristics, such as a sheet of wet strength paper, non-woven fabric and the like, containing a suitable cationic surface active agent to render the substrate electronically attractive to hair soil and moistened with an aqueous solution that facilitates the cleaning operation when the substrate is rubbed on the hair. The solution also may contain ingredients that contribute to management and appearance of the hair after the cleaning operation. The moistened substrate may be, and for convenience preferably is, packaged in a moisture-proof sealed envelope for one-time use. A method for preparing such means comprises incorporating the cationic surface active agent into the substrate, e.g., by addition during manufacture or later impregnation, and moistening the treated substrate with a suitable aqueous solution. An optional step is sealing a moistened piece of the treated sheet-like substrate of suitable size, usually in folded condition, in a moisture-proof envelope.

BACKGROUND OF THE INVENTION

Human hair, in common with other parts of the body, becomes soiled and requires cleaning or shampooing. Personal habits of hair care vary greatly but in general people shampoo their hair only at intervals of several days to a week or two apart. Workers in the art have recognized a need for an in-between hair cleaning means that is simpler and faster than a shampoo and a number of different products for this purpose have been proposed and to some extent produced. While some of these products for cleaning hair between shampoos have found limited use, all of them have been recognized to have deficiencies and disadvantages. The present invention overcomes some of these deficiencies and disadvantages and, in preferred form, provides a small package that can be conveniently carried in a pocket, handbag, briefcase, and the like, readily opened to remove the moistened, fibrous, cation active substrate which is then used for one-time cleaning of the hair and discarded.

DESCRIPTION OF THE INVENTION

The invention has three aspects. One aspect is a method of cleaning hair between shampoos. A second aspect is a means for this purpose as an article of manufacture. A third aspect is methods of producing the hair cleaning means or article.

As a method of cleaning hair between shampoos the invention comprises rubbing the hair with a sheet-like substrate that has been treated to make it electronically attractive to hair soil, i.e., provide a large number of cationic charge sites thereon, in the presence of an aqueous liquid in a moistening amount. By a "moistening amount" is meant a quantity of liquid that is sufficient to loosen hair soil and to wet the substrate to facilitate contact of the loosened hair soil with the cationic charge sites on the substrate but not make the hair so wet that it must be dried before it is coiffured.

As an article of manufacture, the invention is a hair soil removing means comprising a sheet-like substrate that has been treated to provide numerous cation charge sites that are electronically attractive to soil of the type that accumulates on the hair and moistened with a cleaning liquid. Preferably the substrate is in the form of a moist, folded, flexible sheet of absorbent organic fibrous material of suitable wet strength sealed within a tearable, moisture-proof envelope.

The substrate may be any suitable material which is capable of being rendered electronically attractive to soil of the type that accumulates on the hair and which can be held satisfactorily for rubbing over the hair which is to be cleaned. Generally speaking, it will be an absorbent material of fibrous nature and organic origin. By the term "absorbent substrate" is meant a substrate capable of taking up and holding a sufficient quantity of liquid that the portion thereof which is transferred to the hair as the substrate is rubbed on the hair supplies the moistening amount required in cleaning the hair as described above, regardless of the specific mechanism or mechanisms involved in such taking up and holding. Specific materials that are suitable include paper, fabric, both non-woven and woven types, and sponge or sponge-like materials.

Paper is usually made from cellulose fibers derived from wood, rag or cotton, and the like which are laid down from an aqueous suspension in sheet form on a porous screen and then dried. The cellulose fibers from wood are obtained mainly in two forms: (1) ground wood or mechanical pulp, which is merely finely divided wood without purification, and (2) chemical pulp, of which there are three kinds: (a) soda process pulp, obtained from the digestion of wood chips (mostly poplar) by caustic soda; (b) sulfite process pulp (mostly spruce and other coniferous woods) obtained by digestion with a solution of magnesium, ammonium or calcium bisulfite containing free sulfur dioxide; and (c) sulfate process pulp, in which sodium sulfate is added to the caustic liquors but is reduced by the carbon present to the sulfide, which becomes a digesting agent. Sulfite and sulfate pulps (chiefly pine and other coniferous woods) may be bleached or unbleached, but preferably bleached pulp is used. Bleaching is usually done with chlorine gas, chlorine dioxide, or alkaline hypochlorites. Ordinary paper tends to disintegrate when it is re-wetted, which makes it unsuitable for the present invention, but this tendency to disintegrate can be sufficiently inhibited or overcome by incorporating suitable wet strength agents in the paper during the manufacturing process. Any of the many suitable wet strength agents known to those skilled in the art may be used in proper proportions to obtain desired wet strength and absorbency. In general the wet strength agents are either melamine-formaldehyde resins or urea-formaldehyde resins. Of these two resins, melamine-formaldehyde is most commonly and preferably used, particularly since it can be applied as a colloid in the beaters before the paper is made; while the urea-type requires application in the tub sizing before the sheet is formed. The wet strength treatment can increase the strength properties, after immersion in water, of the paper by almost any degree desired, depending upon the amount, kind and method of applying the resin which also affects the absorbency of the paper so that a proper balance of wet strength and absorbency is desirable for the present invention. The amount of wet strength agent may vary within the range of about 0.5 – 5% based on the weight of the fiber. Preferably about 2 – 3% by weight of the melamine type resin is used. A standard test used to measure wet strength in the paper industry is the Mullen test in which a sheet of paper is tested for bursting strength in pounds per square inch of pressure in accordance with ASTM Designation: D- 774-67 (Reapproved 1971) in dry and then in wet condition. A suitable commercialy available crepe paper toweling stock having a stretch of 7 – 10% maximum and a caliper of about 0.006 – 0.007 inch made from bleached sulfate pulp has a Mullen strength of 14 – 16 pounds when dry and of 6 – 7 pounds when wet, i.e., a bursting retention strength of about 35% – 50%, coupled with an absorbency of about 300%, e.g., a piece of dry toweling weighing 1.18 grams after immersing in distilled water, lifting out and draining for 10 seconds weighed 4.8 grams. Paper having absorbencies in the range of about 150 – 400%, preferably about 250–325%, when so tested may be used in the invention. The invention is not limited to the use of wet strength papers containing any particular wet strength agent and any paper having sufficient absorbency and wet strength to resist disintegration on storage of the substrate in a moist environment in an envelope or on use as a hair cleaning instrument is satisfactory for the present invention.

Wet strength paper may also be produced in various types of surface finish from very smooth to somewhat rough in feel and the rough effect can be intensified by various forms of embossing and creping. In general paper used in the present invention preferably has the rough finish rather than the smooth, e.g., crepe toweling stock, because of its greater effectiveness as a cleaning instrument when it is rubbed over the hair.

Non-woven fabrics, in general, are of two main types, felts and bonded webs, produced by laying down a sheet of fibers from suspension usually in air but sometimes in, or assisted by, water. In felt-type fabrics the fibers are sufficiently entwined to hold together without binding agents but the fabrics used in the present invention are preferably the bonded web type in which the fibers are bonded together where they contact each other or at spaced bonding zones by the use of various resins, usually synthetic resins as hereinafter described. For producing a non-woven fabric having the characteristic hand and drape of a woven textile fabric, a starting layer, sheet or base web is laid down using material fibers such as cotton, flax, wood, silk, wool, jute, asbestos, ramie, "rag", or abaca; mineral fibers such as glass; artificial fibers such as viscose rayon, cupra-ammonium rayon, ethyl cellulose or cellulose acetate; synthetic fibers such as polyamides, i.e., nylon, polyesters, i.e., "Dacron", acrylics, i.e., "Orlon", "Acrilan" and "Dynel", polyethylene, vinylidene chloride, i.e., Saran, polyvinyl chloride, polyurethane, etc., alone or in combination with one another. Preferably, organic fibers are used rather than mineral fibers; and viscose rayon has been found to give excellent results in producing the fabric for use in this invention. While relatively long textile-type fibers above normal papermaking lengths and close to normal textile length, say of about ¼ inch to 2 inches or longer, are preferred, shorter fibers, below ¼ inch in length and within the papermaking range, may be used. It is preferred that if the shorter papermaking fibers are used they be unbeaten or substantially unhydrated but shorter hydrated fibers of woodpulp in a papermaking length, for instance, may be mixed with longer fibers in such a way that the longer fibers will contribute to the strength desired in the resulting fabric while the shorter wood fibers will decrease its cost. Acceptable results can also be obtained with suitable proportion of hydrated woodpulp fibers which introduce elements of a plastic mass into the fibrous sheet. Mixtures of fibrous materials, natural and/or synthetic, alone or in combination with resinous and similar plastic particulate materials, arranged in the layer at random (helter-skelter) or in more or less oriented form, such as carded web form, can be used. Satisfactory rearranged webs may be produced from fibrous starting webs weighing between about 80 grains/sq. yd., or slightly lower, and about 1200 grains/sq. yd., or even higher. Any suitable adhesive bonding materials or binders may be employed in aqueous or nonaqueous media to strengthen the web. Water-softenable materials such as beaten cellulose jellies of woodpulp, caroa, ramie, etc.; natural gums including karayo, locust bean, gum arabic and others; starches; and synthetics, such as polyvinyl alcohol, carboxymethylcellulose, polyvinyl acetate which are sometimes employed are preferably not used because the desired wet strength may be lacking but binders or adhesive materials softenable by solvents other than water, exemplified by polyvinyl chloride and polyvinyl butyral and their copolymers, may be used. Preferably, however, either non-reversible and/or thermoplastic binders are used. Nonreversible binders which may be used include urea-formaldehyde and melamineformaldehyde condensation products which are in a lower stage of condensation, i.e., the formation occurs before they are set. Thermoplastic binders which may be used include ethyl cellulose, nylon 6, nylon 11, other nylons, polyvinyl chloride, polyvinyl butyral, polyvinyl formal, plasticized cellulose acetate, polyethylene, polyurethane, polystyrene and the like. The optimum binder content for a given fabric depends upon a number of factors including the absorbency of the fibers, the nature of the binder material, the size and shape of the binder members and their arrangement in the fabric, the nature and length of the fibers, total fiber weight, and the like, from 2% to 35%, usually at least 5% and preferably 6 – 15%, of binder based on fiber weight is satisfactory. By rearranging the fibers as laid down, and by application of the binder in various patterns, non-woven fabrics may also be manufactured with various types of surface appearances and characteristics varying from quite smooth and continuous to quite rough and honeycomb, preference in the present invention being for those with a honeycomb character, i.e., patterns of holes and applied spots of binder giving a somewhat rough finish.

Woven fabrics such as cotton, rayon, nylon, etc. also can be used in the present invention but in general they are not as satisfactory in use as wet strength paper and non-woven fabrics because they are more expensive and, unless they are hemmed at nonselvage edges which further increases the cost substantially, they lack the integrity or coherency characteristic of wet strength paper and non-woven fabric and will leave lint-like particles on the hair which is unacceptable to users.

Sponge material in sheet-like form can also be used in the present invention, both natural and synthetic sponges, but natural sponge has to be used in relatively thick sections in order to have sufficient strength and coherency to withstand the forces generated in rubbing the substrate over the hair to be cleaned. Even synthetic sponge usually has to be used in somewhat thicker sections than is necessary for wet strength paper and non-woven fabric so that such papers and fabrics, in general, are preferred for the present invention because a substrate of suitable size for use can be less bulky and less expensive than if the substrate is made from natural or synthetic sponge.

The material used to make such substrates electronically attractive to soil of the type which accumulates on the hair may be any suitable cationic, organic polyelectrolyte, particularly those which have a high ratio of cationic charge sites to molecular weight. The substrates without treatment normally tend to be anionic, i.e., to have anionic charge sites. The electronic attraction between the anionic substrate and the cationic treating agent makes the agent substantive to the substrate and the excess of cationic charge sites causes the treated substrate to be electronically attractive to hair soil which is generally anionic.

The substrate may be treated with the polyelectrolyte in any suitable way, e.g., the polyelectrolyte may be incorporated in the substrate during manufacture thereof, or the substrate may be impregnated with the polyelectrolyte by immersing it in a solution thereof, or the polyelectrolyte may be included in the cleaning liquid placed in a moisture-proof envelope with the substrate in such amount that it will be exhausted by depositing on the substrate prior to use to clean the hair.

When used to impregnate such substrates, or to deposit thereon from the cleaning liquid, such cationic polyelectrolytes form an adherent surface coating on the anionic fibrous organic substrate material as mentioned above due to the electrostatic attraction between the substrate and the polyelectrolyte material. It is important that only a portion of the total cationic charge sites of the polyelectrolyte be neutralized in this bonding action to the substrate so as to leave positively charged sites available to attract and hold the soil that accumulates on the hair and which is to be removed therefrom when the substrate is rubbed over the area of the hair to be cleaned.

Cationic polyelectrolytes which are especially efficacious for use in treating the substrate for use in the invention are those prepared by the polymerization of $C_1$ to $C_4$ alkylenimines, e.g., ethylenimine, to form polyalkylenimines of suitable molecular weight range, usually from about 600 – 100,000, preferably about 40,000 – 60,000. The bonding action between the substrate and the impregnant makes the impregnant substantive to the substrate so that it is not removed to any substantial degree after it is deposited thereon from solution by rinsing the substrate in water or other aqueous medium.

Other suitable cationic, organic polyelectrolytes for use in treating the substrate for use in accordance with the invention include those prepared by the condensation reaction of dihaloalkanes with polyalkylenepolyamines, e.g., ethylene dichloride and triethylenetetraamine, polyvinylbenzyltrimethyl ammonium chloride, dimethylaminoethyl polymethacrylate, copolymer of N - 2 - hydroxyethyl aziridine and bis (3 - aziridinyl-2-hydroxy-n-propyl)ether, poly (quaternary amines) such as quaternary ammonium polymers, and the like.

These cationic, organic polyelectrolytes are well known to workers skilled in the art and do not form part of the present invention which is not concerned with the polyelectrolytes as such but rather with the use of any suitable polyelectrolyte for imparting to the substrate the property of electronically attracting soil of the type which accumulates on human hair.

The proportion of cationic polyelectrolyte to substrate is not critical provided the treated substrate has a generally cationic character that makes it electronically attractive to hair soil and the amount necessary to provide this character will vary with the particular substrate and cationic polyelectrolyte material used. In general at least about 0.01% is necessary and more than about 2% is unnecessary, based on the weight of the substrate.

The cleaning liquid that moistens the cation active substrate while it is being rubbed over the area of the hair to be cleaned has a number of functions. One function is to contribute substantially to the removal of soil from the hair. Another function is to bring the loosened soil into contact with the free cation charge sites in and/or on the substrate which tends to adhere tenaciously to the soil once this contact has been established. A further beneficial effect in the hair cleaning operation is that it moistens the hair only slightly, as contrasted with the thorough wetting of the hair which occurs when it is given a shampoo and which necessitates a drying operation before the hair can be coiffured. In the slightly moistened state of the hair, cleaned in accordance with the present invention, it is in ideal condition to be coiffured without drying, including setting, particularly by the use of hot curlers.

A particularly preferred cleaning liquid for use in the invention comprises a 25% solution of ethanol in water. Other readily soluble lower monohydric alcohols, advantageously of 2 – 4 carbon atoms, may be substituted in whole or in part for ethanol and the proportion of alcohol can vary from 0 – 50% or more by weight of the solution. In general, however, it is preferred to have an alcohol content of about 10 – 40%, preferably about 20 – 30%.

The cleaning liquid may also contain small amounts, e.g., within the range of 0.1 – 2%, of surface active agents to help loosen the dirt, especially non-ionic agents which are not sticky, e.g., ethoxylated $C_8$ - $C_{20}$ alkanols and organosilicone block copolymers of polysiloxanes and polyoxy alkylenes, emollient materials such as polysiloxanes, mineral oil and the like, other hair conditioning agents, brighteners, perfume and the like, as those skilled in the art will understand.

The proportion of cleaning liquid to substrate is not critical. In general where the substrate which serves as the applicator and liquid are packaged together in a moisture-proof envelope the amount of liquid used is not higher than the absorbency limit of the enclosed applicator so that when the envelope is torn open and the applicator is removed to rub on the hair substantially all the liquid is removed from the envelope on the applicator. The absorbency limit of different substrates varies but with the preferred substrates the limit may be as high as 200 – 500% by weight of the substrate. If the amount of liquid is less than about 20% of the weight of the substrate it may be necessary to use more than one applicator to get the desired cleaning and conditioning of the hair for the coiffure.

The envelope materials suitable for optional use in the present invention include any suitable moisture-proof sheet like material that can be joined in liquid tight relation around the substrate, e.g., a material that can be heat sealed by bringing the two surfaces to be joined into contact with each other and applying heat thereto. A preferred material is a metal foil, such as aluminum foil, coated on the surface to be joined to another like surface with a thermoplastic film such as polyethylene, polyvinyl resin, cellulose acetate and the like, and laminated on the other surface to a sheet of paper to strengthen the foil and provide a printing surface, but materials other than such metal foil laminates including paper, fabric and other cellulosic materials coated with plastic, preferably thermoplastic, material, plastic sheets or films made from various synthetic plastics, coated if necessary or desired with thermoplastic materials, and the like may be utilized for making up the envelope material for use in the invention.

Envelope materials of the type just described are relatively expensive compared with the other components of the article of manufacture and for reasons of economy it is desirable to use the minimum amount of envelope material necessary for making an acceptable package for the substrate. This can be achieved quite satisfactorily in practice by making the substrate of such material as paper and non-woven fabric in sheet form which can be folded for packaging and in use it is unfolded to large enough size to be easily handled in the cleaning operation. A sheet of about 50 – 225, preferably 80 – 200, square inches has sufficient surface area to effectively pick up the soil from the hair and can hold sufficient impregnating liquid to leave the hair in the desired slightly moistened condition. Satisfactory sizes may vary from about 7 inches minimum on a side up to a maximum of about 14 inches, e.g., 8×14, 12×12 and 14×14. In the event that the hair is long and presents more surface than a single piece of moist substrate can effectively clean and condition for coiffure, two or more pieces can be used. A particularly satisfactory size is about 12 inches by 12 inches and by folding it longitudinally and transversely along a plurality of fold lines it can be reduced to a multilayer pad of small enough dimensions to be economically packaged in a heat sealed moisture-proof envelope of the type described. For example, a sheet in open condition having a size of 12 by 12 inches weighing about 4 grams can be folded along 5 lines in the longitudinal direction and 3 lines in the transverse direction to form a 24 layer pad of 2 by 3 inches which can be readily inserted by automatic machinery into an envelope of 4 by 4½ inches having a heat selaed area at the sides and bottom about ¼ inch wide, can then be impregnated with about 15 grams of liquid before it is heat sealed along the open top edge by a heat seal ¼ inches wide.

The method of making the article of manufacture involves a number of steps or operations on the components after these have been selected in accordance with the principles set forth hereinabove and for convenience the description of the method will be illustrated in connection with a preferred embodiment comprising a non-woven rayon fabric substrate impregnated with polyethylenimine (PEI), moistened with a 25% aqueous ethanol liquid and packaged in an envelope made from an aluminum foil - polyethylene laminate.

The non-woven rayon fabric substrate is preferably supplied in the form of a roll having a width corresponding to one of the dimensions of the piece of substrate to be used in each package of the invention. The substrate is first impregnated with the PEI by immersing it in a 0.5% solution of PEI in water followed by thorough rinsing and drying. This deposits about 0.5% by weight of PEI in the impregnated fabric to provide a large number of cationic charge sites on the fabric surface to attract the anionic soil particles to the impregnated substrate when it is contacted with the hair to be cleaned. The weight of the cationic material added to the substrate may vary widely, as stated above, e.g., from about 0.01% – 2%, preferably about 0.25% – 0.5% by weight of PEI based on the initial weight of the fabric. In practice it will be satisfactory if the fabric is immersed once by passing it through an aqueous solution of PEI at a concentration of 0.05–1.0%, preferably 0.5%, and then rinsing, e.g., three times to remove any unattached PEI.

The laminate for the envelopes is also preferably supplied in the form of a roll which may be fed through a machine for forming open topped envelopes by folding the strip centrally into a V-shape, heat sealing the bottom and sides to form open topped envelopes and moving the successive envelopes past a stuffing station where the individual pieces of substrate are introduced one by one into the open topped envelopes. Those skilled in the art know that automatic machinery is available for pulling substrate material from a roll, folding it longitudinally, severing lengths therefrom, folding them transversely and stuffing them one by one into the individual envelopes, moving each stuffed envelope to a filling station where the aqueous liquid is injected through the open top into the envelope, and then heat sealing the open top to make a moisture tight package. This sequence of steps is not essential, however, as it is also practicable to inject the liquid into the envelope prior to the stuffing in of the folded substrate or part of the liquid can be injected into the envelope before and part after the stuffing operation and any sequence may be followed which is found in practice to give satisfactory results.

Heat sealing the edges of the envelope material as described is the preferred way of providing a stable moisture-proof package but the invention contemplates all other ways of producing moisture tight edge seals that resist loosening by the contents of the envelope, e.g., sealing the edges with water and/or alcohol resistant adhesives, and the like.

The process of sealing moistened substrate sheets in envelopes as just described results in a package embodying the invention in the form in which it is most conveniently used because such packages can be carried in a pocket, a handbag, a briefcase, a suitcase and the like without damage to the packages or things near them and even after a long period of storage an applicator is available for immediate use. It may be used by simply tearing open the enevelope, taking it out of the opened envelope, unfolding it and rubbing it over the area of the hair to be cleaned.

Other ways of preparing the substrate for use as a hair cleaning means, however, are practical and contemplated by the invention. For example, the substrate can be cut into sheets of suitable size and packaged in any convenient type of cardboard container, box or the like and the moistening liquid can be packaged separately in suitable concentrations and composition in glass, plastic or like containers, including squeeze bottles, for moistening a sheet taken from its container at time of use. Thus, the liquid in suitable amount to moisten a sheet of substrate can be poured from a glass or plastic container into a shallow dish such as a soup bowl, the sheet can be dipped in the liquid to moisten it and then applied directly to the hair in the manner previously described. Instead of dipping a sheet into a dish containing liquid, a squeeze bottle can be used to spray liquid onto a sheet until it is suitably moistened for rubbing the hair to clean it. Alternatively, the hair can be sprayed with the aqueous liquid to moisten it and a sheet taken from the cardboard container can be rubbed without separately moistening it on the moist hair to clean it in the manner described. Moistened sheets can also be packaged in bulk packs in suitable moisture-proof containers from which they can be drawn one by one for use as described.

The effectiveness of the present invention in removing soil from the hair is easily seen by even a casual observer by carrying out the hair cleaning operations described herein which transfers soil from the hair to the applicator sheet where it is visible as darkened or discolored areas.

After the cleaning operation the hair is left in an ideal condition for putting up in the form of coiffure that the user prefers. For those who prefer to wear their hair straight it is in ideal condition for combing. For those who prefer curled hair, the cleaned hair in the slightly moistened condition is ideal for putting up on rollers or for curling with a hot curling iron.

The following examples are given for the purpose of illustrating but not limiting the invention:

EXAMPLE I

Part I, prepare a liquid comprising:

| | |
|---|---|
| Ethanol (SD40-190 proof) | 25.00% |
| Perfume (Rose fragrance) | 0.05% |
| Deionized water | 74.95% |

Adjust pH to 4.0 ± 0.1 using citric acid (usually requires about 0.004%)

Part II, prepare a towelette or an applicator from all purpose non-woven perforated fabric having a thickness of about 0.011 inch average and within the range of about 0.008 – 0.016 inch, a dry breaking strength of about 14.4 pounds MD and a wet breaking strength of about 5.9 pounds, MD, composed of rayon fibers of 1.5 denier intermittially bonded by continuous, wavy, transverse synthetic resin stripes or bands, by cutting off a sheet of about 12 × 12 inch. Such sheets have an average weight of about 4.6 grams (about 4 minimum and 5.5 maximum). The towelette or applicator sheet is soaked in a 0.5% aqueous solution of polyethylenimine having a molecular weight within the range of about 40,000 – 60,000 (Dow PEI-600), rinsed three (3) times in deionized water and dried in air or a clothes drier. It contains about 0.5% PEI. The breaking strength is determined in accordance with standard methods of testing non-woven fabrics ASTM Designations: D-1117-69 and D-1682-64 (Reapproved 1970) using the cut strip method in the machine direction (MD), using 1×6 inch strips.

Part III, prepare an envelope from an aluminum foil-paper, polyethylene laminate about 4×4.5 inch heat sealed along a ¼ inch edge band at both sides and bottom. Fold the towelette on five (5) longitudinal fold lines into an accordion folded strip of six (6) 2 × 12 inch panels and then fold this strip twice at the mid point each time, i.e., on three (3) transverse fold lines to form a pad of twenty-four (24) panels of about 2 × 3 inch each. Insert the pad into the envelope, add 15 grams of the liquid of Part I and seal the open side of the envelope by heat over an edge band about ¼ inch wide.

EXAMPLE II

Part I, prepare a liquid comprising deionized water containing about 0.05% water-soluble fragrance adjusted to pH 4 ± 0.1 by addition of citric acid.

Part II, prepare a towelette as described in EXAMPLE I using a bleached crepe toweling stock made from sulfate pulp containing about 3% melamine resin as a wet strength agent. The paper has a caliper of about 0.006 – 0.007 inch, a Mullen strenght of 14 – 16 pounds dry and of 6 – 7 pounds wet. The 12 × 12 inch applicator weighs about 4 grams when dry. It is soft, resistant to shredding and linting, has a stretch of about 7% – 10% maximum, a minimum brightness of 78 by standard reflectance test, no disagreeable odor dry or wet and an absorbency of about 300% i.e., when immersed in distilled water, lifted out and drained for 10 seconds it will weigh about four (4) times as much as it weighed when dry. After soaking in the 0.5% PEI solution and drying it contains about 0.5% PEI by weight.

Part III, prepare an envelope as described in EXAMPLE I, fold and insert the paper towelette through the open top, add 15 grams of the liquid prepared in Part I and seal the open top by heat over an edge band about ¼ inch wide.

Instead of impregnating the towelette with PEI as described in EXAMPLES I and II as a preliminary step to folding the towelette for insertion into the envelope where the liquid of Part I is added, the towelette can be inserted into the envelope without impregnation and the PEI can be added to the liquid of Part I. For example, if about 0.05% PEI based on the weight of the solution is added to Part I of EXAMPLE I, it is exhausted from the 15 grams of solution within 24 hours and premanently bound to an approximately 4 gram non-woven towelette moistened therewith in the envelope. The towelette contains about 0.2% PEI based on the dry weight of the towelette. If the amount of PEI is increased to 0.1% by weight of the solution, some free PEI is left in the solution even after the towelette has been sealed in the envelope for six (6) weeks, which is undesirable, so that the limit in the amount of PEI that will be fully exhausted under the conditions set forth is above 0.05 and under 0.1% PEI in the solution. Towelettes prepared by this method are used and function in the same way as towelettes prepared according to EXAMPLES I and II.

A further way of making a substrate electronically attractive to hair soil is to incorporate therein a cationic polyelectrolyte during the process of manufacture. At any suitable stage in the manufacture of wet strength paper and non-woven fabric the polyelectrolyte may be added in the desired proportions to the fibers. If the fibers are laid down wet the polyelectrolyte may be dissolved in the aqueous phase from which it will be withdrawn by the fibers as described above. If the fibers are laid down dry the polyelectrolyte may be added in finely divided form which will go into solution when the sheet is first exposed to an aqueous medium and from the solution thus formed it will be withdrawn by the substrate in the manner already described.

In summary the method of preparing the article of the invention comprises the steps or operations of:

1. Treating a coherent sheet-like, wet strength organic fibrous material to make it electronically attractive to hair soil. This may be done by incorporating a cationic polyelectrolyte in the substrate during manufacture, by impregnating the substrate with the polyelectrolyte in the liquid that moistens the substrate in a moisture-proof package, and any equivalent thereof.

2. Moistening the sheet-like substrate at or before the time it is rubbed on the hair to clean it with a suitable aqueous liquid to assist in loosening the hair soil and bringing the loosened soil into contact with the cationic charge sites of the polyelectrolyte on the substrate where it is held by the electronic attraction between these cationic charge sites and the negative charges on the soil. Preferably the liquid is an aqueous alcohol which may contain one or more of the additives mentioned above and equivalents, although when the substrate is packaged in a moisture-proof envelope alcohol is not an essential ingredient.

3. Optionally sealing the moistened substrate, when the article is made in its most convenient form, within a moisture-proof envelope, preferably by heat, after the substrate has been folded longitudinally and transversely into a multilayer pad, inserted into the envelope and moistened with the aqueous liquid.

Although the invention has been described and illustrated in connection with certain preferred embodiments, it will be understood by those skilled in the art that modifications and variations may be made without departing from the principles of the invention as herein described and exemplified.

Having thus described and exemplified the invention, what is claimed is:

1. An article of manufacture suitable for removing hair soil between shampoos comprising a coherent, sheet-like, fibrous, absorbent substrate having bonded to its surface at least .01% by weight of a cationic, organic polyelectrolyte selected from the group consisting of polymers of $C_1$-$C_4$ alkylenimines and quaternary ammonium polymers, said polyelectrolyte having numerous charge sites thereon to render it electronically attractive to soil, which is moistened with at least about 20% by weight of an aqueous $C_2$-$C_4$ alcoholic cleaning liquid.

2. An article of manufacture as set forth in claim 1 wherein said polyelectrolyte comprises polyethylenimine having a molecular weight in the range of 600 to 100,000.

3. An article of manufacture as set forth in claim 1 wherein said polyelectrolyte is present in an amount within the range of about 0.1 to 2% by weight of said sheet.

4. An article of manufacture as set forth in claim 1 wherein said cleaning liquid includes 0.1 to 2% by weight of a surface active agent.

5. An article of manufacture as set forth in claim 3 in which said polyethlenimine is present in an amount within the range of 0.2 to 0.5% and has a molecular weight in the range of about 40,000 to 60,000.

6. An article of manufacture as set forth in claim 1 in which said substrate is a sheet selected from the group consisting of of wet strength paper and non-woven fabric.

7. An article of manufacture as set forth in claim 1 in which the aqueous cleaning liquid contains about 25% ethanol.

8. An article of manufacture as set forth in claim 6 in which said substrate is a folded wet strength sheet of organic fibers enclosed within a tearable, moisture-proof envelope.

9. An article of manufacture as set forth in claim 8 in which the envelope comprises a laminate of aluminum foil, paper and polyethylene heat sealed at the edges.

10. The method of making an article for cleaning hair between shampoos which comprises the steps of treating a coherent, absorbent, wet-strength, sheet-like substrate of organic fibrous material with at least .01% by weight of a cationic polyelectrolyte selected from the group consisting of polymers of $C_1$-$C_4$ alkylenimines and quaternary ammonium polymers whereby said polyelectrolyte is bonded to said sheet and makes the sheet electronically attractive to hair soil due to the numerous positively charged sites thereon, and moistening the sheet with at least about 20% by weight of an aqueous $C_2$-$C_4$ alcoholic liquid.

11. The method of making an article of manufacture for cleaning the hair between shampoos as set froth in claim 10 in which the polyelectrolyte is a polyethylenimine having a molecular weight in the range of 40,000 to 60,000.

12. The method of making an article of manufacture for cleaning the hair between shampoos as set forth in claim 10 in which the polyelectrolyte is incorporated in the substrate by immersing it in an aqueous solution of the polyelectrolyte, thoroughly rinsing the substrate and drying it.

13. The method of making an article of manufacture for cleaning the hair between shampoos as set forth in claim 10 in which said substrate is a folded sheet, said folded sheet is inserted into an envelope of heat sealable, tearable, moisture-proof material into which the aqueous alcoholic liquid is flowed and said envelope is thereafter heat sealed.

14. The method of making an article of manufacture for cleaning the hair between shampoos as set forth in claim 13 in which the polyelectrolyte is incorporated in the substrate by adding the polyelectrolyte to the moistening liquid in an effective proportion that is exhausted onto the substrate within a day.

15. The method as set forth in claim 13 in which said sheet is selected from the group consisting of wet strength paper and non-woven fabric.

16. The method of cleaning hair between shampoos which comprises rubbing the hair with a coherent, absorbent sheet-like substrate of organic fibrous material having bonded to its surface at least .01% by weight of a cationic, organic polyelectrolyte selected from the group consisting of polymers of $C_1$-$C_4$ alkylenimines and quaternary ammonium polymers, said polyelectrolyte having numerous cationic charge sites thereon, in the presence of an aqueous liquid in moistening amount of at least about 20% by weight of said substrate.

17. The method as set forth in claim 16 in which the aqueous liquid contains ethanol within the range of 0 to 50% by weight.

* * * * *